United States Patent [19]

Deger et al.

[11] Patent Number: 5,437,981
[45] Date of Patent: Aug. 1, 1995

[54] METHOD FOR THE IMMUNOLOGICAL DETERMINATION OF LIGANDS

[75] Inventors: Arno Deger, Seeshaupt; Roland Schenk, Weilheim; Gerhard Bienhaus, Haunshofen, all of Germany

[73] Assignee: Boehringer Mannheim GmbH, Mannheim-Waldhof, Germany

[21] Appl. No.: 887,587

[22] Filed: May 20, 1992

Related U.S. Application Data

[63] Continuation-in-part of Ser. No. 656,393, Feb. 15, 1991, abandoned.

[30] Foreign Application Priority Data

Feb. 26, 1990 [DE] Germany ............... 40 06 054.3

[51] Int. Cl.$^6$ ............... G01N 33/536; G01N 33/542; G01N 33/532; G01N 33/53
[52] U.S. Cl. ............... 435/7.1; 435/7.5; 435/7.9; 435/7.92; 435/7.93; 435/7.94; 436/543; 436/547
[58] Field of Search ............ 435/6, 7.1, 7.5, 7.92, 435/7.93, 7.9, 7.94; 436/500, 501, 512, 518, 532, 536, 538, 543, 547

[56] References Cited

U.S. PATENT DOCUMENTS

| | | | |
|---|---|---|---|
| 4,228,237 | 10/1980 | Hevey et al. | 435/7.5 |
| 4,870,007 | 9/1989 | Smith-Lewis | 435/28 |
| 4,935,339 | 6/1990 | Zahradnik | 435/5 |
| 4,945,042 | 7/1990 | Geiger et al. | 435/7.5 |
| 5,082,935 | 1/1992 | Cruickshank | 536/27 |
| 5,126,241 | 6/1992 | Schenk | 435/7.1 |
| 5,130,234 | 7/1992 | Hoshino et al. | 435/7.9 |
| 5,196,351 | 3/1993 | Harris et al. | 436/501 |
| 5,277,589 | 1/1994 | Schmitt et al. | 436/518 |

FOREIGN PATENT DOCUMENTS

| | | |
|---|---|---|
| 0019277 | 11/1980 | European Pat. Off. |
| 0160900 | 11/1985 | European Pat. Off. |
| 0363942 | 4/1990 | European Pat. Off. |

OTHER PUBLICATIONS

Tijssen, P., *Practice and Theory of Enzyme Immunoassays*, p. 341 (1985).
Tijssen, "Practices and Theory of Immunoassays", Elsevier, N.Y., pp. 340–342 (1985).
Chen et al., "$T_3$ Uptakes," *Clinical Chemistry*, Ed Kaplan et al., pp. 1170–1173 (1984).

*Primary Examiner*—Michael P. Woodward
*Attorney, Agent, or Firm*—Felfe & Lynch

[57] ABSTRACT

Method for the immunological determination of a ligand in which the ligand to be determined is reacted with a) at least 2 molecules of a specifically bindable substance P2 of which at least one of these molecules carries a label and b) a receptor R which consists of a binding partner P1 which is capable of monovalent binding to P2 and a binding site $R_1$ for the ligand to be determined and then the label is determined, as well as a reagent for the immunological determination of a ligand which contains a specifically bindable substance P2 which is present at least partially in labelled form and a receptor R which consists of a binding partner P1 which is capable of monovalent binding to P2 and a binding site $R_1$ for the ligand to be determined.

10 Claims, 2 Drawing Sheets

METHOD FOR THE IMMUNOLOGICAL DETERMINATION OF LIGANDS

This application is a continuation-in-part of application Ser. No. 656,393, filed Feb. 15, 1991, abandoned.

The invention concerns an immunological method for the determination of a ligand as well as a suitable reagent composition therefor.

Very many substances occur in body fluids and tissues which are capable of binding to a specific binding partner and serve as parameters for particular diseases or for the state of health of the human body. These include, on the one hand, immunologically active proteins which have binding sites on their surface such as e.g. tumour markers, hormones or viral proteins and, on the other hand, DNA fragments. Since these substances, which are denoted "ligand" in the following, often only occur in very small amounts, they are detected using methods which are based on immunoassays by which these substances can be determined very specifically and exactly. The known immunological methods of determination may be classified into homogeneous and heterogeneous procedures. In the heterogeneous procedures a solid phase reaction is always involved in order to immobilize complexes containing the substance to be detected and a labelled constituent and thus to separate them from unbound constituents. In homogeneous methods no separation of bound label and unbound label is carried out so that differentiation between bound and unbound label must be effected by other methods.

The heterogeneous immunoassays are mainly based on two variants namely competitive and sandwich assays. In these variants of the method at least two receptors are usually employed which are capable of binding to the ligand to be detected and of which one carries a label and the other is bound to a solid phase or mediates the binding to the solid phase. A multitude of variants for this are known in which further receptors are used. All complexes which are bound to the solid phase and which are labelled then enter into the determination.

Basically there are two variants for carrying out competitive heterogeneous immunoassays in which either an antibody to the ligand is immobilized or a substance analogous to the ligand is immobilized. In the first variant a sample solution containing the ligand and a conjugate of ligand and a label is incubated with the immobilized antibody. In this process ligand and labelled substance compete for the binding to the antibody. The more ligand is present in the solution the less labelled substance can be bound. After separating the solid and liquid phase the label can then be determined in one of the two phases. The amount of bound labelled substance is an indirect measure for the amount of substance to be determined and thus of ligand.

In the second variant the sample solution containing the ligand is incubated with an antibody which is specific for it and with the immobilized analogue of the substance. In this process the immobilized ligand and the ligand present in the solution compete for binding to the antibody. The more ligand is present in the solution the less antibody is bound to the solid phase via binding to the immobilized ligand analogue. Also in this case, after separating the solid phase from the liquid phase, the amount of bound label is determined which again is indirectly proportional to the amount of ligand in the sample solution.

In the variants of the sandwich immunoassay an antibody against the ligand is immobilized and the sample solution is incubated in the presence of this immobilized antibody together with a further antibody which is capable of binding to the ligand and is labelled. In this process the receptors are added in excess so that all molecules present in the sample which are to be detected are bound to the solid phase and bind to a labelled receptor.

A disadvantage of this method is that for each substance (ligand) to be determined several specially adapted receptors have to be provided. Thus, labelled special antibodies are often necessary which are different from ligand to ligand. The covalent binding of labelling groups to antibodies, which usually attack at several sites on the antibody molecule, can result in undesirable changes in the binding properties of the thus modified antibody.

A further problem occurs when testing for proteins or DNA or RNA fragments which have more than one binding site.

In these cases a majority or a multitude of receptors can bind whereby the resulting inaccuracy may still be compensated by using standards. This inaccuracy is, however, potentiated when all the receptors used are themselves bivalent or polyvalent.

It was therefore the object of the invention to provide a method with which ligands can be detected with high accuracy, good reproducibility and high specificity and in which, in addition, universally applicable labelled constituents and universally suitable solid phase materials can be used. In particular, only one single specially adapted receptor should be required.

This object is achieved by a method for the immunological determination of a ligand which is characterized in that the ligand to be determined is reacted with a) at least 2 molecules of a specifically bindable substance P2 of which at least one of these molecules carries a label and
b) a receptor R which consists of a binding partner P1 which is capable of monovalent binding to P2 and a binding site $R_1$ for the ligand to be determined and then the label is determined.

According to characteristic a) labelled P2 is used in a known amount and preferably in excess with respect to the possible amount of ligand whereby this excess relates to the double stoichiometric amount of ligand if all of P2 is labelled and to the single stoichiometric amount of ligand if unlabelled P2 is also used. In the latter embodiment unlabelled P2 is also present in a one-fold excess.

The method according to the present invention is suitable for the determination of all ligands to be detected in body fluids or tissue extracts which are capable of a specific binding whereby substances in low concentrations can be detected just as well as those in high concentrations. The sensitivity and accuracy of the method is improved compared to the hitherto known methods. The invention allows rapid and reliable determinations to be carried out with simple reagents.

The method is particularly suitable for determining ligands with several binding sites and DNA or RNA molecules. In this connection, a specific binding site is understood as a binding site which can participate in a specific binding to another substance. Examples of this are antigenic determinants, specific binding sites on proteins or a specific nucleic acid sequence on DNA or RNA.

An important feature is that receptor R contains a single partner P1 of the specific binding pair P1/P2 and this partner P1 is monovalent with respect to P2 so that only a single molecule P2 can be bound per molecule of receptor R. Substances are suitable as component $R_1$ which are capable of specific binding to the ligand. These can be e.g. macromolecules such as antibodies, antibody fragments and specifically bindable binding proteins, haptens, epitopes or, in the case of a DNA or RNA test, DNA probes. The component $R_1$ preferably has only one binding site for the ligand. In the case of a protein test it is preferable to use antibody fragments which only have one paratope or substances which bind specifically to the protein, for example T4 for the detection of T4 binding protein. For the detection of DNA or RNA, a probe is for example used as component $R_1$ which can hybridize with a sequence of the DNA or RNA to be detected. An Fab fragment of an antibody capable of specific binding to the ligand is especially preferred as the component $R_1$ in the receptor R. Depending on the ligand, $R_1$ can be a uniform substance or a mixture. The component P1 of the receptor R is a partner of a specific binding pair. Pairs which can specifically bind to one another are known. Suitable binding partners are especially biotin-streptavidin or avidin; hapten-antibody, antigen-antibody, concanavalin-antibody; sugar-lectin; hapten-binding protein, e.g. thyroxine binding globulin and thyroxine antibodies or oligopeptide antibodies.

Biotin and streptavidin or avidin are particularly preferably used as the binding pair so that receptor $R_1$ especially preferably contains a single molecule of biotin as partner P1.

The production of the conjugates is carried out using methods known to the expert (e.g. in analogy to Eur. J. Biochem. 131 (1980) 333–338).

In the case of a heterogeneous procedure P2, in a non-labelled form, mediates the binding to the solid phase.

In accordance with the present invention, the provision of a universal test is achieved since solid phase and labelled conjugate can remain the same for all determinations and only a single receptor has to be matched to the respective ligand to be detected. Since the binding of R, ligand and labelled P2 takes place in a homogeneous phase it is preferred over the binding of R to the solid phase P2 which proceeds in a heterogeneous phase. The unlabelled P2 of the specific binding system which is bound to the solid phase is therefore used in excess.

Conjugates are preferably used as receptor R which consist of an antibody or antibody fragment $R_1$ and biotin as P1.

The production of the conjugates R is carried out in a known manner by reaction of the component $R_1$ e.g. of an antibody or antibody derivative, with the partner P1 in a stoichiometric 1:1 ratio. This coupling reaction preferably takes place via a free SH group or amino group. The products which form statistically in this process containing two or more components P1 can be separated by gel chromatographic methods. For the method according to the present invention conjugates R are particularly preferably used which consist of an Fab' fragment and biotin. In order to produce such conjugates an antibody capable of binding to the ligand to be detected is treated for example with pepsin, the F(ab')$_2$ fragment formed is subjected to reducing conditions and is subsequently reacted with the component P1 whereby the component P1 binds to a free SH group or amino group of the Fab' fragment either via a funcional group present in the component P1 or via a spacer, if desired after activation of the binding sites. Products which contain one or more partners P1 can be separated for example according to one of the procedures described in EP-A 0 313 343 in which the separation is based on the difference in charge of related proteins. If the partner binds via the amino groups of a protein then single or several-fold binding leads to conjugates of different charge which enables their separation.

Particularly suitable as the solid phase are test tubes or microtitre plates made of polystyrene and similar plastics the inner surfaces of which are coated adsorptively or covalently with P2. Particulate substances are also suitable e.g. molecular sieve materials, glass beads, plastic tubing and similar materials as well as porous carriers in a layer form such as paper. The binding of the partner P2 is carried out in a known way.

At least a portion of P2, in the homogeneous test procedure all of P2, is employed in a labelled form. The usual labels for immunological tests are suitable as the label e.g. an enzyme, a fluorescent, chemiluminescent or radioactive substance. Methods for labelling are known to the expert e.g. from Clin. Chim. Acta 81 (1977) 1–40 and do not need to be described here in further detail. The label can be determined in a known way.

If the invention is used with a homogeneous test procedure, i.e. without use of a solid phase, then all of P2 is used in a labelled form. The complexes which form in this process of ligand, at least two molecules R and a number of molecules of P2 corresponding to the number of R in the complex are labelled and then detected by methods known to the expert for measuring a label in homogeneous test procedures. Suitable methods of detection are described for example in EP-B 0084.

When carrying out the method according to the present invention in a heterogeneous as well as in a homogeneous way a conjugate C can be used in addition which contains the ligand or a ligand analogue with a binding partner P1 which is identical to the binding partner P1 in the receptor R. In this procedure ligand in the sample solution competes with ligand or ligand analogue in the added conjugate C for the component $R_1$ in the receptor R so that a competitive method results. This embodiment can be applied to solid phase methods as well as to methods in a homogeneous phase. The details of the production of the receptor R apply in the same way to the production of the conjugate C. In this connection a substance is regarded as the ligand analogue which has similar properties to the ligand itself with regard to capability of binding to component $R_1$ in the receptor R so that under the stoichiometric conditions employed competition does indeed take place for the binding site.

The method can be carried out in one or more steps. The evaluation is carried out in a known way. Since each of the receptors and also the substance to be determined can only react specifically with its own particular reaction partner it is possible to incubate all receptors and the sample together and to carry out the method in one step. This is particularly advantageous when carrying out the method in an automated analyser. If the method is to be carried out heterogeneously in one step then substance P2 which carries a label is preferably employed in a limiting amount compared to receptor R.

All variants of the method are preferably carried out in a buffered solution. Buffer systems for this method are generally known. GOOD buffers and phosphate buffers are particularly suitable for this.

In order to carry out the method according to the present invention in a heterogeneous phase the sample solution is incubated either simultaneously or sequentially with the three receptors R, labelled P2 and, if desired, C in the presence of a solid phase coated with unlabelled P2. In this process two receptors R bind for example to the ligand via the component $R_1$. Labelled P2 is then bound via partner P1 of the one receptor R and binding to the solid phase occurs by means of the binding pair P1/unlabelled P2 via the other receptor R. All complexes which are bound to the solid phase and which carry a label enter into the evaluation.

According to the present invention a method is provided which is simple and which can be carried out rapidly and which is very sensitive even when using polyclonal antibodies.

The present invention also provides a reagent for the immunological determination of a ligand which is characterized in that it contains a specifically bindable substance P2 which is present at least partially in labelled form and a receptor R which consists of a binding partner P1 which is capable of monovalent binding to P2 and a binding site $R_1$ for the ligand to be determined. The reagent preferably contains the substance P2 in a labelled form and in a form bound to a solid phase in a combined formulation (e.g. a layer in a test carrier device or magnetic particle solution).

According to a preferred embodiment this reagent contains unlabelled P2 bound to a solid phase or capable of binding to a solid phase. According to a further preferred embodiment the reagent contains in addition a conjugate C of ligand or ligand analogue and a component P1 as defined above.

This reagent is suitable for the determination of a multitude of parameters in body fluids and tissue extracts.

In a preferred embodiment the reagent contains in addition buffer substances. It particularly preferably contains phosphate buffers or GOOD buffers.

BRIEF DESCRIPTION OF THE FIGURES

FIG. 1 shows a diagram in which the results for the determination of the thyroxine binding index are plotted.

FIG. 2 shows a diagram in which the results for the determination of anti-T4 antibodies are plotted.

Figure 1:
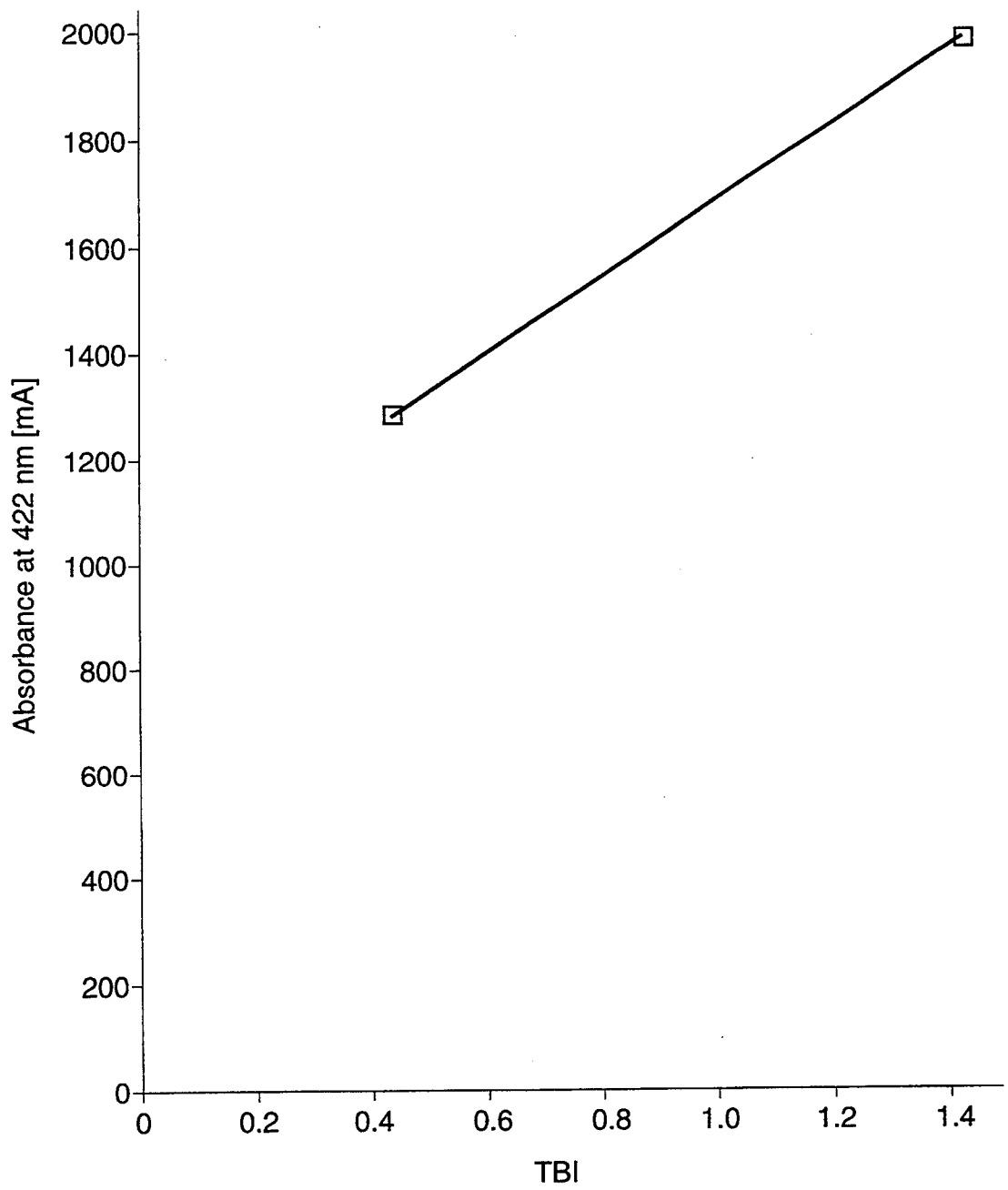
FIG. 1—shows a diagram in which the results for the determination of thyroxine binding index are plotted.

The invention is elucidated by the figure and by the examples.

EXAMPLE 1

Determination of AFP ($\alpha$-foetal protein)

a) Production of a conjugate of biotin and Fab' fragments of anti-AFP antibodies (anti-AFP-Fab'-biotin)

Polyclonal antibodies against AFP are purified immunosorptively and Fab' fragments are produced therefrom. These are coupled to biotin according to Analyt. Biochem. 161 (1987) 262-271 or Analyt. Biochem. 149 (1985) 529-536.

b) Test procedure
Buffer A:
120 mmol/l sodium barbiturate
18.2 mmol/l phosphate buffer, pH 8.6
1.27 mmol/l 8-anilino-1-naphthalinesulfonic acid
0.2 % by weight bovine serum albumin (final concentration in the test)

50 $\mu$l sample (human serum supplemented with AFP) is added to 480 $\mu$l buffer A and 20 $\mu$l anti-AFP-Fab'-biotin (final concentration in the test: 4 $\mu$g/ml) in a polystyrene vessel coated with streptavidin (produced according to EP-A 0 269 092hereby incorporated by reference) and incubated for 30 minutes at 25° C. Subsequently 480 $\mu$l buffer A and 20 $\mu$l of a solution of a streptavidin-POD conjugate (50 mU/test) is added and incubated for 30 minutes at 25° C. It is washed and 1 ml ABTS ® solution (9.1 mmol/l ABTS ®, 2,2'-azino-di[3-ethylbenzthiazoline sulfonic acid (6)]di-ammonium salt, 100 mmol/l phosphate-citrate buffer, pH 4.4, 3.2 mmol/l sodium perborate) is added, incubated for 30 minutes at 25° C. and the optical density is determined at 422 nm as a measure for the AFP content.

EXAMPLE 2

T-uptake test

The determination is carried out in such a way that T4 is added to the sample in order to saturate excess TBG. The unbound T4 is then measured. A calibration curve is thus obtained which is directly proportional to the thyroxine binding index (TBI).

Sample: standards containing defined amounts of TBG and T4 in human serum are used as standards. A TBI of 0.44 is obtained for sample 1 and a TBI of 1.44 for sample 2 (cf. instructions for the Enzymun Test ® DTBK of Boehringer Mannheim GmbH, order no. 249416).

Reagent 1
100 U/l conjugate of streptavidin and POD
36 pmol/l T4
120 mmol/l sodium barbiturate
18.2 mmol/l phosphate buffer, pH 8.6
0.2% by weight bovine serum albumin Reagent 2
0.2 nmol/l conjugate of T4 and biotin
0.15 mg/l anti-T4-Fab'-biotin of polyclonal antibodies against T4 (produced according to Example 1)
120 mmol/l sodium barbiturate
18.2 mmol/l phosphate buffer, pH 8.6
0.2% by weight bovine serum albumin 50 $\mu$l sample are added to 500 $\mu$l reagent 1 in a polystyrene vessel coated with streptavidin and incubated for 30 minutes at 25° C. 500 $\mu$l reagent 2 are added and incubated for 30 minutes at 25° C. Subsequently it is washed with water and 1 ml ABTS ® solution (cf Example 1) is added, incubated for 30 minutes at 25° C. and the optical density is determined at 422 nm as a measure for the thyroxine binding index. The results are shown in FIG. 1.

EXAMPLE 3

Determination of an antibody against T4

Standard solutions of polyclonal antibodies against T4 having the concentrations 0, 0.5 and 1.0 mg/l are used as sample.

Figure 2:
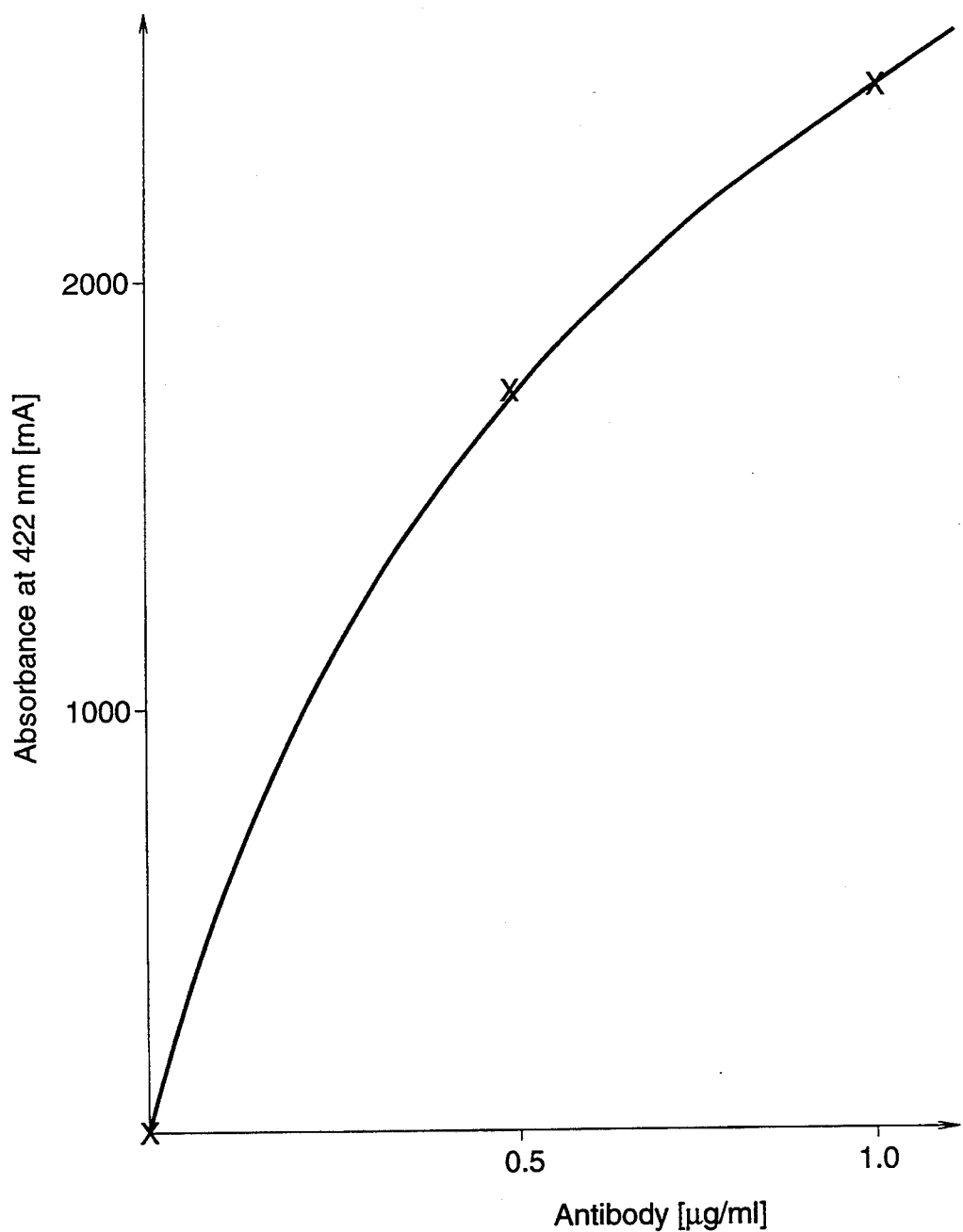
FIG. 2—shows a diagram in which the results for the determination of ant-T4 antibodies are plotted.

Reagent:
10 mmol/l T4 biotin conjugate
50 U/l streptavidin-POD conjugate
120 mmol/l sodium barbiturate
18.2 mmol/l phosphate buffer, pH 8.6
1.27 mmol/l 8-aniline-1-naphthalinesulfonic acid 0.2% by weight bovine serum albumin 50 μl sample and 1 ml reagent are incubated for 30 minutes at 25° C. in a polystyrene vessel coated with streptavidin. Subsequently it is washed and 1 ml ABTS® solution (cf Example 1) is added, incubated for 30 minutes at 25° C. and the optical density is determined at nm as a measure for the content of antibodies against T4. The results are shown in FIG. 2.

EXAMPLE 4

Preparation of IgG biotin (1:1)

1) 50 mg of a monoclonal antibody against TSH (ECACC 87122202) is reacted with a 2-fold molar excess of D-biotinyl-ε-amidocaproic acid-N-hydroxysuccinimide ester according to JACS 100 (1978), 3585–3590. Monobiotinylated IgG's are obtained as the main product and higher biotinylated side products which are separated off.

2) The separation is carried out by DIP chromatography (Delta-Isoelectric-Point) which is described e.g. in EP-A 0131 343

The separation of the mixture is carried out on a Mono-S cation-exchange column (Pharmacia).

The mixture was applied in 1 mmol/l potassium pyrophosphate buffer pH 6.9 (buffer A). The bound components were eluted by the application of a linear gradient with 20 mmol/l potassium pyrophosphate buffer/200 mmol/l NaCl, pH 6.9 (buffer B). The pure monobiotinylated IgG fraction is obtained in a high yield as well as pools with a higher degree of biotinylation.

EXAMPLE 5

Preparation of Fab-biotin (1:1)

1) Monoclonal antibodies against TSH (ECACC 87122202) are cleaved to Fab according to A. Johnstone, R. Thorpe; Immunochemistry in Practice, Blackwell Scientific Publications (1982), 52–53.

50 mg Fab are reacted as described in Example 4.

2) The cleavage is carried out here under modified conditions:

Buffer A: 50 mmol/l MES pH 5.6
Buffer B: 50 mmol/l MES/200 mmol/l NaCl pH 5.6
Under these conditions pure Fab-biotin can be obtained in high yields.

Abbreviations:
Biotin X-OSu:
N-biotinoyl-ε-aminocaproic acid-hydroxysuccinimide ester
MES:
2-(N-morpholino)-ethane sulfonic acid
KPP: potassium pyrophosphate
BSA: bovine serum albumin
POD: peroxidase

EXAMPLE 6

TSH test

The test is carried out with a mixture of the two monoclonal antibodies against TSH (ECACC 87122201 and ECACC 87122202) which were prepared as Fab-biotin according to Example 5.

EXAMPLE 7

A homogeneous test for AFP

50 μl sample is incubated for 15 minutes at 37° C. with 20 μl phosphate buffer (18.2 mmol/l pH 8.6, 10% polyethylene glycol 6000), 20 μl conjugate of anti AFP-Fab'-biotin of polyclonal antibodies against AFP ($1 \times 10^{-7}$ mol/l cf example 1 and 20 ul conjugate of streptavidin and POD ($2 \times 10^{-7}$ mol/l), 2.5 ml of a solution of 0.5 mmol/l 4-aminoantipyrine, 50 mmol/l phenol and 35 mmol/l hydrogen peroxide are added and incubated for 5 minutes at 37° C. The optical density is determined at 500 nm as a measure for the content of AFP.

EXAMPLE 8

A heterogenous test using an antigen/antibody system

50 μl sample, 980 μl buffer A (example 4) and 20 μl anti-AFP-Fab'-digoxigenin (end concentration in the assay 2 μg/ml) were mixed in a polystyrol tube which was coated with a polyclonal antibody against digoxin and digoxigenin. The mixture was incubated at 25° C. for 1 hour. The tube was washed and 1 ml anti-digoxin-antibody-POD conjugate (activity of POD 60 mU/ml) was added in buffer A and incubated for 1 hour at 25° C. After washing, 1 ml of ABTS solution (cf. example 1) was added and incubated for 30 minutes at 25° C. The optical density at 422 nm was measured for determination of the AFP content.

The synthesis of anti-AFP-Fab'-digoxigenin was carried out according to Clin. Chem. (1986) 32:1639 hereby incorporated by reference.

Step 1:

3 μg Fab-biotin mixture in 1 ml 50 mmol/l phosphate buffer pH 7.5, 0.1% BSA are incubated for 2 hours with 200 μl sample (human serum supplemented with TSH) in a tube coated with streptavidin (Example 1, see AFP). Afterwards the unbound material is washed out.

Step 2:

200 mU streptavidin-POD conjugate in 1 ml buffer (see above) is incubated for 1 hour and subsequently the unbound material is washed out.

Step 3:

1 ml substrate solution (Example 1, see AFP) is incubated for 1 hour and the optical density is determined at 422 nm as a measure for the TSH content.

It will be understood that the specification and examples are illustrative but not limitative of the present invention and that other embodiments within the spirit and scope of the invention will suggest themselves to those skilled in the art.

We claim:

1. Method for determining a ligand via a homogeneous assay, comprising:

contacting a sample with an amount of a labelled substance $P_2$, and a receptor R which consists of one molecule of a binding partner $P_1$, which monovalently and specifically binds to $P_2$, and one molecule of $R_1$, which immunologically binds to said ligand, to form complexes comprising $P_1$, $P_2$, $R_1$ and said ligand, and determining said complexes as a determination of said ligand in said sample.

2. Method for determining a ligand in a heterogeneous immunoassay, comprising:

(i) contacting a sample with a receptor R consisting of one molecule $P_1$ and one molecule $R_1$, and a substance $P_2$ immobilized on a solid phase, wherein $P_1$ and $P_2$ specifically bind to each other and $R_1$ immunologically binds to said ligand, to immobilize said ligand on said solid phase via interaction of R and $P_2$, (ii) contacting said sample with labelled $P_2$ after said ligand has been immobilized, wherein said labelled $P_2$ binds to any R bound to said ligand which is not also bound to said immobilized $P_2$, and (iii) determining labelled $P_2$ bound to said solid phase as a determination of said ligand in said sample.

3. The method of claim 1, wherein said homogeneous assay is a competitive assay and further comprises adding to said sample a conjugate C which consists of (a) a member of the group consisting of a molecule of ligand and a molecule of ligand analogue and (b) a molecule of $P_1$, wherein said conjugate C completes with any ligand in said sample for binding to $R_1$.

4. The method of claim 2, wherein said heterogeneous assay is a competitive assay and further comprises adding to said sample a conjugate C which consists of (a) a member of the group consisting of a molecule of ligand and a molecule of ligand analogue and (b) a molecule of $P_1$, wherein said conjugate C completes with any ligand in said sample for binding to $R_1$.

5. The method of claim 1, wherein $P_1$ is biotin, a hapten, or an epitope.

6. The method of claim 2, wherein $P_1$ is biotin, a hapten, or an epitope.

7. The method of claim 1, wherein $P_2$ is a member selected from the group consisting of avidin, streptavidin, a streptavidin polymer, an antibody, an Fab antibody fragment, and an F(ab')$_2$ antibody fragment.

8. The method of claim 2, wherein $P_2$ is a member selected from the group consisting of avidin, streptavidin, a streptavidin polymer, an antibody, an Fab antibody fragment, and an F(ab')$_2$ antibody fragment.

9. The method of claim 1, wherein $R_1$ is a member selected from the group consisting of a hapten, an epitope, and a macromolecule.

10. The method of claim 2, wherein $R_1$ is a member selected from the group consisting of a hapten, an epitope, and a macromolecule.

* * * * *